United States Patent [19]
Pellegrini et al.

[11] 3,930,838
[45] Jan. 6, 1976

[54] S-BENZYL-N,N-DISEC-BUTYLTHIOCARBAMATE AND ITS USE AS A RICE FIELD HERBICIDE AND A RICE GROWTH STIMULANT

[75] Inventors: Giovanni Pellegrini; Giuseppe Losco; Antonio Quattrini, all of Milan; Emilio Arsura, S. Donato Milanese (Milan), all of Italy

[73] Assignee: Montecatini Edison S.p.A., Milan, Italy

[22] Filed: Dec. 14, 1973

[21] Appl. No.: 424,767

Related U.S. Application Data

[63] Continuation of Ser. No. 178,662, Sept. 8, 1971, abandoned.

[30] Foreign Application Priority Data
Sept. 10, 1970   Italy ................................ 29546/70

[52] U.S. Cl. ...................... 71/100; 47/57.6; 71/88; 71/111; 71/118; 71/124; 71/DIG. 1; 260/455 A

[51] Int. Cl.$^2$.......................................... A01N 9/12
[58] Field of Search.................... 71/100; 260/455 A

[56]   References Cited
UNITED STATES PATENTS

| | | | |
|---|---|---|---|
| 3,632,332 | 1/1972 | Maeda ................................ 71/100 |
| 3,679,726 | 7/1972 | Kudamatsu et al. .................. 71/100 |
| 3,682,616 | 8/1972 | Kimura et al. ......................... 71/100 |

FOREIGN PATENTS OR APPLICATIONS

| | | | |
|---|---|---|---|
| 1,269,029 | 6/1961 | France ............................ 71/DIG. 1 |

*Primary Examiner*—Glennon H. Hollrah
*Attorney, Agent, or Firm*—Hubbell, Cohen, & Stiefel

[57]       ABSTRACT

S-benzyl-N,N-disec.butylthiocarbamate, a new compound, has the unique combination of properties of being both an efficient rice field weed killer and a rice growth stimulant.

14 Claims, 2 Drawing Figures

1  2  3    4   5   6

7  8  9   10  11  12

S-BENZYL-N,N-DISEC-BUTYLTHIOCARBAMATE AND ITS USE AS A RICE FIELD HERBICIDE AND A RICE GROWTH STIMULANT

BACKGROUND OF THE INVENTION

1. Field of the Invention

This is a continuation of application Ser. No. 178,662, filed Sept. 8, 1971 and now abandoned.

The present invention relates to a particular compound of the class of benzyl-N,N-dialkylthiocarbamates, which compound has not heretofore been described in the literature, namely, S-benzyl-N,N-disec.-butylthiocarbamate. The invention also relates to the use of this compound to stimulate rice growth while at the same time killing the weeds growing in the rice fields, as well as to compositions containing the compound and their utilization.

In the herbicide field, research has been carried out for many years throughout the world in an effort to find very effective products which exert a highly specific action, namely the killing of weeds while leaving undamaged the useful, structurally similar agricultural plants. Such products, moreover, should be characterized by a particular balance of properties, as they must associate specificity of action (selectivity) with other characteristics, including low toxicity towards warm-blooded and cold-blooded animals, degradability in soil, activity persistence, and relatively low manufacturing cost.

A complete specificity of action is particularly difficult to attain when the weed control is carried out on cultivations of useful plants which are very similar, from a botanical viewpoint, to the infesting plants to be killed and, consequently, more likely to be damaged by the herbicides.

Such specificity is particularly required for weeding rice from the most common and noxious infesting weeds hindering its growth, such as *Panicum spp.*, and *Echinocloa spp.*, in particular the latter graminaceous plant which, at least during its early life periods, also is very similar to rice morphologically.

Of course, it is advisable to kill the infesting weeds as early as possible, that is, during the very first periods of the rice growth. However, the weed killing under these conditions is particularly difficult since the herbicide also easily attacks the rice seedlings. Besides, there are also some environmental difficulties when the weeding is conducted in submerged cultures.

2. Description of the Prior Art

Among the herbicides which are employed to weed rice during its pre-emergence period, ethyl-1-hexamethylene-imino-carbothiolate, known under the common name of "molinate" (ISO) has come into common use.

However, even treatments with this widely utilized compound, carried out in submerged cultures during pre-emergence, may shock the rice seedlings and casue growth retardation which can vary in duration and degree and sometimes also affects the harvest.

Belgian Pat. No. 728,265 discloses and claims, for selective weeding in rice fields, the use of compositions containing, as the principle active ingredients compounds having the general formula

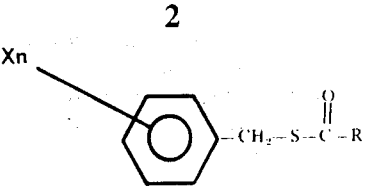

wherein
R is monoalkylamino or dialkylamino; and
X is chlorine, bromine, or methyl. One of the preferred compounds is S-(4-chlorobenzyl)-N,N-diethylthiocarbamate,

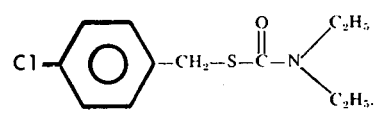

These products too are not free from toxicity towards the useful plant, so that they cannot be suitably utilized in rice fields before sowing, but only 7–10 days after the rice transplantation, so that the herbicide comes into contact with the useful plant when the plant has already gotting over the transplantation crisis and has grown enough so as not to be affected by the herbicide.

In the above cited patent, the monothiocarbamates having a substituent in the benzyl ring are compared with the analogous unsubstituted (in the benzyl ring) monothiocarbamate, S-benzyl-N,N-diethylthiocarbamate, which latter compound is shown to be less active towards the weeds and more aggressive towards the rice.

There is also other patent literature disclosing the use of benzyl lower alkyl thiocarbamates as weed killers. Particularly pertinent are U.S. Pat. Nos. 2,919,182; 2,992,091 and 3,144,475 to Harman and D'Amico. The latter patent discloses and claims benzyl dibutylthiocarbamate as a weed killer. However, as already indicated, nowhere in the literature have we been able to find any indication of the unique properties of the particular compound of the present invention, S-benzyl-N,N-disec.butylthiocarbamate.

SUMMARY OF THE INVENTION

We have now surprisingly found that the characteristics of being an efficient herbicide towards rice field weeds and of stimulating the rice growth are exceptionally combined in S-benzyl-N,N-disec.butylthiocarbamate, a new product not yet described in the literature.

Accordingly, the present invention provides a compound which is capable of weeding a rice field in an efficient and at the same time thoroughly safe way, avoiding any possible damage to the useful plant. The compound of the present invention also has the unusual property of simultaneously stimulating the growth of the useful plant to thereby put it in the best condition to most quickly overcome the environmental adversities of both physical and biological nature, and to strengthen the inherent capabilities of the plant to absorb and assimilate nourishment. In addition, the product of the present invention is a versatile weed killer, that is, a weed killer capable of giving good results under the most diverse climatic conditions and adaptable to the most diverse cultivation techniques. Accordingly, the present invention affords increased production and the realization of a considerable saving in seed, for a given investment.

On the basis of the literature and prior knowledge in the art, this discovery was thoroughly unexpected because of the aggressiveness of similar compounds which are not substituted in the benzene ring towards rice.

S-benzyl-N,N-disec.butylthiocarbamate is a liquid, oily product which is practically insoluble in water, and soluble in most of the organic solvents such as, for example, benzene, ether, heptane, methanol, cyclohexanone, acetone, methyl chloride, and dichloroethane. It has the following characteristics:

$$d_{23}^{4} = 1.044 \qquad n_{D}^{25.5} = 1.5325$$

boiling point = 130° to 132°C at 0.1 mm. Hg.

BRIEF DESCRIPTION OF THE DRAWING

In the drawing, FIG. 2 is a sketch similar to FIG. 1 but showing the relative results when a 6 kg./hectare dose is employed. The experimental data upon which FIGS. 1 and 2 are based is reported hereinafter in Example 11.

DESCRIPTION OF THE PREFERRED EMBODIMENTS

Figure 1:
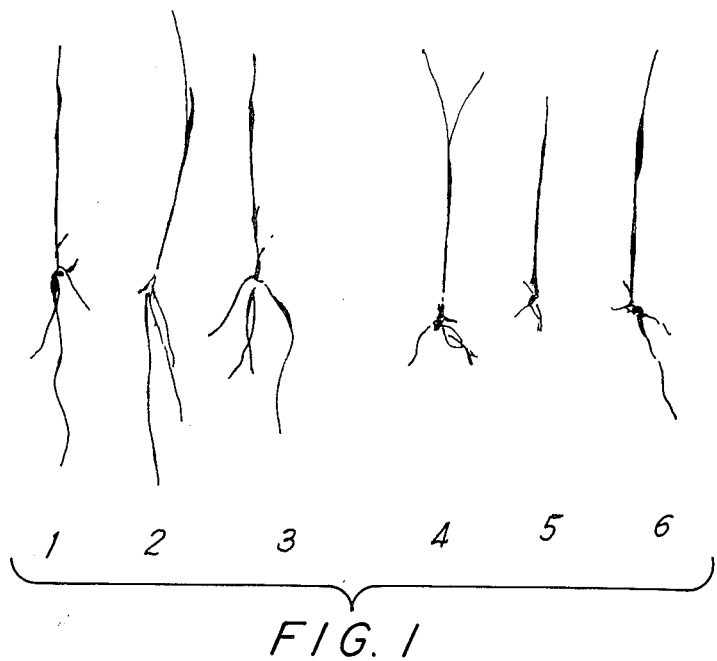
FIG. 1 is a sketch comparing the growth of rice 21 days after treatment with a 4 kg./hectare dose of the product of the present invention with that of an untreated control.

S-benzyl-N,N-disec.butylthiocarbamate can be prepared by means of known reactions for compounds of this class, of which the following are examples:

1. Reaction between disec.butylcarbamoyl chloride and benzyl mercaptan:

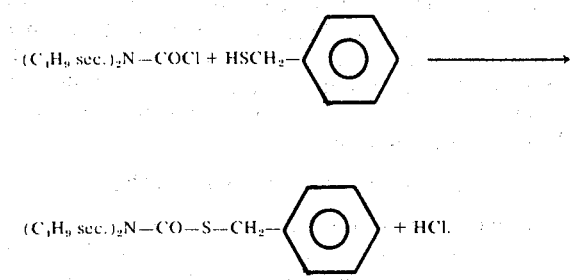

One operates in an inert solvent or diluent. A tertiary base (for instance pyridine) is used as an HCl acceptor. Alternatively, one may use the mercaptan in the form of a salt, e.g., the sodium salt, which can be obtained from the reaction of the mercaptan with sodium metal or, even better, with caustic alkali in an aqueous medium, and subsequent dehydration.

2. Reaction between disec.butylamine, carbon oxysulfide, NaOH and a benzyl halide (e.g., benzyl chloride), according to the following equation:

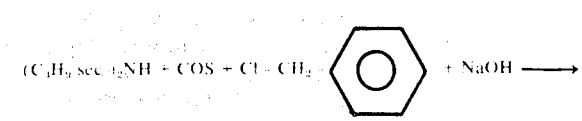

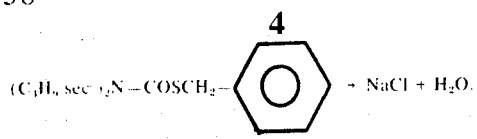

The reaction may be easily conducted by reacting the carbon oxysulfide with the amine in the presence of the stoichiometric quantity of caustic alkali (for instance NaOH), in a first step. The disec.butylthiocarbamate thus formed is reacted, in situ, with the benzyl halide, in a second step.

3. Reaction between benzylthiocarbonyl chloride (a product already known from Chem. Berichte 80 pages 2293–2301, 1956) and disec.butylamine:

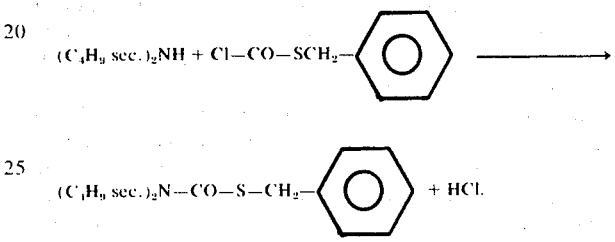

This reaction can be carried out in the presence of an inert solvent (for instance: benzene, ether, dichloroethane). The HCl can be neutralized either by a second mole of amine or, more suitably, by caustic alkali (for instance, NaOH in aqueous solution).

The following detailed examples are presented to further illustrate our invention.

PREPARATION

Example 1

2.3 G. of sodium metal (0.1 mole) cut into small pieces were suspended in 25 ml. of anhydrous benzene. 18.6 G. (0.15 mole) of benzyl mercaptan were added and the mixture heated under countercurrent stirring until gas generation ceased. 19.1 G. (0.1 mole) of disec.butylcarbamoyl chloride were then added, and the heating continued under reflux for 2 hours. After cooling to 20°C, the sodium chloride which formed was removed by filtration, and the benzene solvent was evaporated at 50° to 60°C under a reduced pressure of about 15 mm. Hg. The residue was then distilled under a pressure of 0.1 mm. Hg. and the fraction distilling at 130°–132°C was recovered. 20 G. of S-benzyl-N,N-disec.butylthiocarbamate were thus obtained.

Analysis: $N_{found} = 4.90\%$; $N_{calculated} = 5.01\%$. $S_{found} = 11.50\%$; $S_{calculated} = 11.47\%$.

Disec.butylcarbamoyl chloride has not yet been described in the chemical literature. It has been prepared by reacting phosgene with disec.butylamine as follows:

250 G. (2.5 moles) of phosgene were absorbed, at about 5°C, under thoroughly anhydrous conditions, in 1,000 ml. of anhydrous benzene. 645 G. of anhydrous disec.butylamine (5 moles) were subsequently added under stirring, while keeping the temperature at 0° to 5°C. A voluminous white precipitate consisting of amine hydrochloride thereupon formed.

Stirring was continued for about 3 hours, and then 500 ml. of ice water introduced in order to dissolve the precipitate. The two liquid phases thus formed were separated. The organic phase was washed with 500 ml. of ice water, then dried over $CaCl_2$ and concentrated under reduced pressure (15 mm. Hg.) at 50° to 60°C.

The resulting liquid (450 G.) was distilled under high vacuum. 425 G. of disec.butylcarbamoyl chloride were thus obtained, having distilled at 85° to 90°C at 0.1 mm. Hg. The yield was 89% of the theoretical value.

Analysis: $Cl_{calculated}$ = 18.5%; $Cl_{found}$ = 18.22 to 18.33%.

Example 2

1,000 Ml. of benzene, 205 G. of benzylmercaptan (1.65 moles) and 66 G. of NaOH (1.65 moles) dissolved in 500 ml. of water were introduced into a 3 l. flask provided with stirrer, thermometer, reflux condenser and a device for azeotropic distillation. The mixture was heated to boiling while stirring, and the water was thoroughly eliminated azeotropically. 316 G. (1.65 moles) of disec.butylcarbamoyl chloride were then added and the heating continued at reflux for 4 hours while continually stirring.

After cooling to 20°C, 1,000 ml. of water were added and the two liquid phases separated. The benzene phase was washed twice with 500 ml. of water each time and then concentrated under reduced pressure (15 mm. Hg.) at 50° to 60°C. 415 G. of S-benzyl-N,N-disec.butylthiocarbamate were obtained by distilling the resulting liquid as described in Example 1 (at a pressure of 0.1 mm. Hg. and a temperature of 130° to 132°C).

Example 3

A mixture consisting of 12.4 G. of benzyl mercaptan (0.1 mole), 7.9 G. of anhydrous pyridine (0.1 mole) and 19.1 G. disec.butylcarbamoyl chloride was heated to 130°C and kept at this temperature for 5 hours.

After cooling, 15 ml. of methylene chloride and 30 ml. of water were added.

The aqueous layer was removed, and the organic layer was then washed with water and concentrated under reduced pressure. By then treating the residue as described in Examples 1 and 2, 13 G. of S-benzyl-N,N-disec.butylthiocarbamate were obtained.

Example 4

27 G. (0.45 mole) of carbon oxysulfide ware bubbled in 2 hours and 30 minutes into a mixture consisting of 49 G. of disec.butylamine (0.38 mole), 15.2 G. of NaOH (0.38 mole) and 165 G. of water, keeping the temperature between 0° and 3°C. Thereafter, 6.6 G. of potassium iodide (0.04 mole) and 50.4 G. of benzyl chloride (0.4 mole) were introduced into the reaction mixture which was then heated under vigorous stirring in a first step to 30°C, kept at this temperature for 2 hours, and then heated in a second step to 50°C and maintained at this temperature for 12 hours. After cooling to room temperature, 250 ml. of methylene chloride were added and a separation was then carried out. The organic liquid phase was washed with water, concentrated at reduced pressure and finally distilled according to the procedure described in Examples 1 and 2. 25 G. of S-benzyl-N,N-disec.butylthiocarbamate were thus obtained.

Example 5

18.6 G. of benzylthiocarbonyl chloride were introduced into a solution consisting of 25.8 G. of disec.-butylamine (0.2 mole) and 150 ml. of anhydrous benzene. An exothermic reaction with formation of disec.-butylamine hydrochloride crystals took place.

The mixture was then heated to 65°C, kept at this temperature for 30 minutes, and then cooled to 20°C. 250 Ml. of water were added and, after separation of the layers, the aqueous layer was removed. This treatment was repeated once more with 250 ml. of water. The organic layer was then treated as described in Examples 1 and 2. 25 G. of distilled S-benzyl-N,N-disec.butylthiocarbamate were thus obtained.

Example 6

18.6 G. of benzylthiocarbonyl chloride (0.1 mole) dissolved in 26 cc. of dichloroethane were added to a solution consisting of 14.2 G. of disec.butylamine (0.11 mole) in 50 cc. of 1,2-dichloroethane, under strong stirring at about 0°C, and then 40 G. of a 10% aqueous solution of NaOH (0.1 mole) were added while maintaining the temperature at 0°C. The cooling bath was then removed and the temperature allowed to rise spontaneously to 20°C. The organic and aqueous layers were then separated. The organic solution was recovered, washed twice with 50 ml. of water and then treated as described in Examples 1 and 2. 21 G. of distilled S-benzyl-N,N-disec.-butylthiocarbamate were obtained.

Weeding

The weeding action of S-benzyl-N,N-disec.butylthiocarbamate hereinafter referred to as M3432) towards several weeds, and in particular towards *Echinocloa spp.* (barnyard grass) occurs when average quantities between about 2 and 6 kg. per hectare, are used. Even when employing only 4 to 6 kg./ha., the stimulating action of M3432 on rice is also very evident, so that an unusual combination of weeding action with stimulating effect towards the useful plant can be achieved. The stimulating effect is exhibited by a more vigorous growth of the plant and a larger development of the root apparatus; no malformations are noticed, while the stand is also increased.

Some data proving the stimulating effects of treatments with M3432 carried out on rice seedlings under different conditions, both in comparison with molinate and with products which are homologues and isomers of M3432, are reported hereinafter. As already indicated M3432 is not only harmless towards the rice, but even stimulates the germination and development of both the root apparatus and the shoot, as is demonstrated in the following examples.

Example 7

Into a set of cylindrical pots having a 200 $cm^2$ internal surface, sieved rice field earth in a quantity of 1 kg. per pot was introduced. After leveling and wetting with 200 cc. of water, the earth surface of the pots was uniformly sprayed with hydroacetone solutions containing, respectively, 0, 0.2, 0.3, and 0.4% active product (a.p.). 4 Ml. of the solution were sprayed onto each pot, so that the amount of active product in a set of four pots was 0, 4, 6, and 8 kg./ha., respectively. Immediately after spraying, each pot was filled with water to a level of 7 cm. over the soil surface. Thereafter, the sowing was carried out at the rate of 15 pre-germinated rice seeds per pot. Three repetitions were performed for each treatment. The pots were kept in an air-conditioned atmosphere with a daily temperature variation between 10° and 25°C and a 14 hour per day light period. After 24 days, the percentage of sprouted plants and the length of the shoot were recorded. The results are reported in Table 1 below.

TABLE 1

Results obtained from a comparative selectivity test on rice performed in a submerged culture, in air-conditioned atmosphere with M3432 and molinate.

| Treatment | Sprouted plants (%) | Average values per plant | |
|---|---|---|---|
| | | Main root (cm.) | Shoot (cm.) |
| Control | 42.3 | 7.0 | 17.2 |
| M3432, 4 kg./ha. | 60.0 | 8.3 | 17.8 |
| M3432, 6 kg./ha. | 53.3 | 10.4 | 21.1 |
| M3432, 8 kg./ha. | 77.7 | 10.1 | 23.9 |
| Molinate, 4 kg./ha. | 42.3 | 7.4 | 15.3 |
| Molinate, 6 kg./ha. | 20.0 | 3.9 | 8.2 |
| Molinate, 8 kg./ha. | 11.0 | 4.6 | 6.6 |

From the data reported in Table 1, the stimulating action exerted by M3432 on rice in submerged culture appears evident, while the molinate exhibits, under the same conditions, a narrow margin of safety, having unfavorably affected the rice plant growth even in quantities of 6 kg./ha.

Example 8

In view of the foregoing results, a further test was conducted according to the methodology of Example 7. During such test, M3432 was employed in quantities of 10, 20, and 30 kg./ha. The results were gathered 33 days after the treatments. The resulting average values are reported in Table 2 below.

TABLE 2

| Treatment | Sprouted plants (%) | Main root (cm.) | Shoot (cm.) | Secondary roots (number per plant) |
|---|---|---|---|---|
| Control | 46.6 | 3.8 | 9.9 | 1.07 |
| M3432 10 kg./ha. | 71.1 | 11.3 | 19.97 | 4.4 |
| M3432 20 kg./ha. | 77.7 | 10.6 | 20.9 | 5.1 |
| M3432 30 kg./ha. | 80.0 | 11.1 | 23.4 | 5.4 |

Example 9a

A test was arranged in a hothouse on a set of boxes having a 1,000 cm$^2$ internal surface. 18 Kg. of sieved rice field earth were put into each box. After leveling, the earth surfaces of each of a set of six boxes were uniformly sprayed with hydroacetone solutions containing, respectively, 0, 0.5, 0.75, 1, 1.25, and 1.5% of M3432. 20 Cc. of solution was sprayed into each box, corresponding to 0, 10, 15, 20, 25, and 30 kg./ha., respectively. Each box was flooded with a 10 cm. water layer measured from the earth surface. The sowing was carried out immediately afterwards with a pre-germinated (cv) RIBE rice seed, employing a quantity of 40 seeds per box.

During the test, the hothouse temperature ranged from +10° to +28°C. 27 Days after the treatment, all the rice plants were recovered from each box and subjected to biometric controls. The average values, based on the 40 rice seeds introduced into each box, are shown in Table 3 below.

TABLE 3

| M3432 (kg./ha.) | Sprouted plants | | Main root | | Shoot | | Secondary roots | |
|---|---|---|---|---|---|---|---|---|
| | % | % of control | cm. | % of control | cm. | % of control | No. | % of control |
| 0 | 40.0 | 100 | 3.10 | 100 | 5.92 | 100 | 2.22 | 100 |
| 10 | 52.5 | 131 | 4.82 | 150 | 11.70 | 198 | 2.82 | 127 |
| 15 | 57.5 | 144 | 4.06 | 131 | 11.99 | 203 | 2.95 | 133 |
| 20 | 77.5 | 193 | 8.29 | 267 | 12.15 | 205 | 4.42 | 199 |
| 25 | 85.0 | 212 | 6.77 | 218 | 16.77 | 283 | 4.66 | 210 |
| 30 | 87.5 | 219 | 8.84 | 285 | 14.59 | 246 | 4.90 | 220 |

Example 9b

A second test was carried out in a hothouse, employing the identical method and under the identical conditions as in Example 9a. The relevant results were gathered 66 days after the treatment had occurred, and are reported in Table 4 below.

TABLE 4

Results gathered 66 days after treatment, obtained from a test with M3432 conducted on rice in flooded culture in a hothouse.

| M3432 (kg./ha.) | Sprouted plants (%) | Main root (cm.) | Shoot (cm.) | Secondary roots (No.) | WEIGHT ON DRY BASIS | |
|---|---|---|---|---|---|---|
| | | | | | Roots (g. per 100 plant) | Shoot (g. per 100 plant) |
| 0 | 30.0 | 7.24 | 10.44 | 5.12 | 2.675 | 4.250 |
| 10 | 45.0 | 12.64 | 16.74 | 12.20 | 5.550 | 8.000 |
| 15 | 45.0 | 13.54 | 18.16 | 13.30 | 6.800 | 11.800 |
| 20 | 60.0 | 17.16 | 26.00 | 21.00 | 10.480 | 18.050 |
| 25 | 40.0 | 10.26 | 15.00 | 10.05 | 4.250 | 6.875 |
| 30 | 40.0 | 8.21 | 14.50 | 8.00 | 2.800 | 5.050 |

Example 10

In the province of Novara, Italy, a test was performed outdoors in clay soil. For each treatment, a 600 m$^2$ plot provided with independent water feed was prepared. After soil working and leveling, the treatment was effected on Apr. 23, 1970, using formulations in emulsifiable oils of M3432 and of molinate, sprayed by means of mechanical devices. Only the plot treated with molinate was harrowed just after treatment in order to incorporate the product and to avoid any losses of same due to volatilization. Immediately afterwards, the plots were flooded to a water level of 10–12 cm.

Pre-germinated cv. RIBE rice was mechanically sowed broadcast on Apr. 25, 1970.

36 Days after the treatment, 50 rice plants were taken at random from each plot and subjected to biometric controls. The average results obtained therefrom are reported in Table 5 below.

TABLE 5

Data found during a test carried out in the open field. Treatment with a water emulsion on a non-flooded soil immediately followed by flooding and by sowing.

| Treatment | Main root (cm.) | Shoot (cm.) | Secondary roots (no.) | AVERAGE WEIGHT PER PLANT CALCULATED ON DRY BASIS | | |
|---|---|---|---|---|---|---|
| | | | | Roots (g.) | Shoot (g.) | Total (g.) |
| Control | 6.46 | 25.99 | 9.50 | 1.675 | 3.273 | 4.948 |
| Molinate 4 kg./ha. | 7.67 | 25.72 | 9.06 | 1.866 | 3.257 | 5.123 |
| M3432 4 kg./ha. | 9.29 | 29.22 | 9.64 | 2.431 | 4.073 | 6.504 |
| M3432 6 kg./ha. | 10.19 | 30.17 | 10.42 | 3.123 | 4.209 | 7.341 |

Periodical checks were carried out on the four plots. The results obtained therefrom two months after the treatment are set forth in Table 6 below.

TABLE 6

| Treatment | (°) Stand | Rice plants appearance | Average height |
|---|---|---|---|
| Control | normal | normal | 40–45 cm. |
| Molinate, 4 kg./ha. | normal | normal | 35–45 cm. |
| M3432, 4 kg./ha. | very high | excellent | about 60 cm. |
| 6 kg./ha. | very high | excellent | about 60 cm. |

(°) Number of tillers per unit of area.

Example 11

Comparison between the stimulating action exerted by M3432 and that exerted by its lower homologues and isomers In the province of Pavia, a test was carried out with outdoor treatments in a loam soil, on rice plots having a 12 m² surface each.

Formulations of 20% M3432 in emulsifiable oil were compared with 20% formulations in emulsifiable oil of S-benzyl-N,N-diisopropyl thiocarbamate; S-benzyl-N,N-diisobutylthiocarbamate; and S-benzyl-N,N-din.-butylthiocarbamate employing quantities of 4, 6 and 20 kg./ha.

For each treatment, the results were gathered on 20 plants 21 days after the sowing.

The values obtained are set forth in Table 7 below.

The data in the foregoing tables demonstrates that M3432 enhances rice growth, stimulating not only the development of the shoots emerging from the earth, but also, and in particular, the development of the roots.

Figure 2:
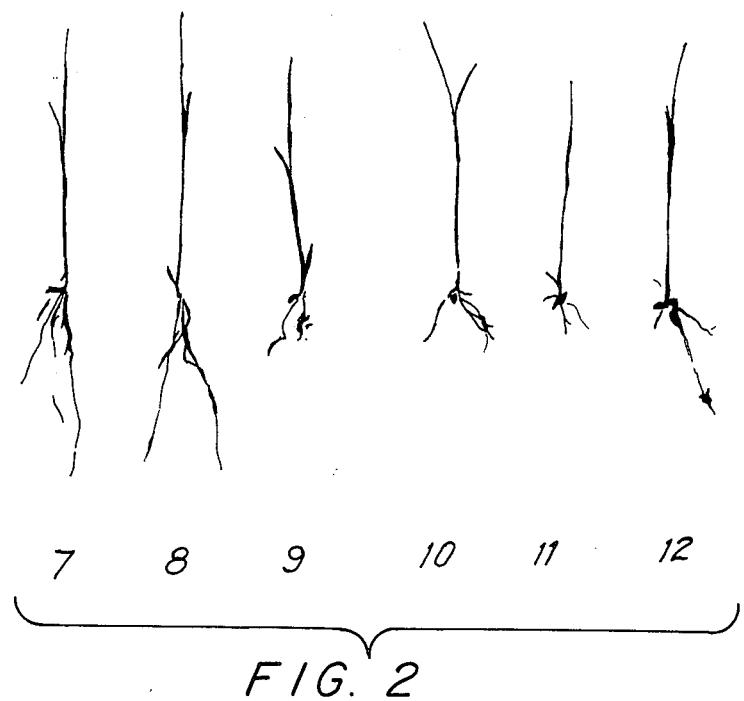

Roots are longer, bigger and more numerous, as is shown in the enclosed drawings, wherein FIG. 1. compares the appearance of the rice 21 days after treatment with a dose of 4 kg./ha. of M3432 (1,2 and 3) with that of an untreated control (4, 5 and 6); and FIG. 2 compares the appearance of the rice 21 days after treatment with a dose of 6 kg./ha. of M3432 (7, 8 and 9) with that of an untreated control (10, 11 and 12).

This growth enhancement does not modify the normal physiology of the plant. There are no malformations which, conversely, do develop when products exerting a para-hormonal action are used. The vegetative apparatus grows according to normal proportions, but the development occurs more rapidly, so that the plant can more quickly overcome biological and physical adversities which it faces during the early stages of its growth.

From an agronomical point of view this discovery is of the utmost importance, as the plant derives immediate and lasting advantages therefrom. The larger development of the roots enables the rice plant to better anchor to the soil and, consequently, to better avoid the danger of being uprooted by the wind, which happens very often in flooded rice fields during the first weeks after sowing. The quicker development of the shoot, especially during the early growth stages, also enables the rice plants to escape more rapidly the suffocating action of the algae which, as is well known, can even prevent the rice from emerging from the water surface.

TABLE 7

| Treatments | Quantity of active product (kg./ha.) | Main roots (No.) | Shoot (cm.) | Secondary roots (No.) |
|---|---|---|---|---|
| Control | | 4.36 | 6.07 | 2.15 |
| M3432 | 4 | 5.55 | 7.11 | 2.52 |
| | 6 | 5.73 | 7.34 | 2.63 |
| | 20 | 6.76 | 7.68 | 2.63 |
| S-benzyl-N,N-diiso-propylthiocarbamate | 4 | 3.45 | 5.36 | 2.52 |
| | 6 | 3.67 | 5.44 | 1.63 |
| | 20 | 2.79 | 4.03 | 1.21 |
| S-benzyl-N,N-diiso-butylthiocarbamate | 4 | 3.21 | 5.25 | 1.68 |
| | 6 | 2.76 | 4.21 | 1.57 |
| | 20 | 2.59 | 3.96 | 1.52 |
| S-benzyl-N,N-din.butyl-thiocarbamate | 4 | 3.26 | 4.76 | 1.78 |
| | 6 | 2.81 | 5.24 | 1.94 |
| | 20 | 1.94 | 2.34 | 2.05 |

The effect of the M3432, which stimulates the development of the shoots as well as that of the roots, lasts long, thus allowing the rice plants to get stronger, to shoot better and to better utilize the fertilizers introduced into the soil. It follows that, in the soil treated with the product of the present invention, it is possible to use fewer seeds per hectare to achieve equivalent results to those presently achieved without M3432. Also, the fertilizers are better utilized as they are more easily and quickly absorbed.

It follows that the product of the present invention can be suitably employed in mixture with the fertilizers commonly used in rice growing, as it indirectly magnifies the efficacy of the fertilizers and enables the plant to better utilize them.

To increase the stimulating action, it may be advisable, from an economical viewpoint, to employ the product in quantities far exceeding those sufficient for effective weeding, although the product, as already noted, exerts a highly stimulating effect even in these lower quantities. With such increased stimulation it may be suitable also to use larger quantities of fertilizers in order to influence the rice production in the best possible way.

The possibilities of utilization outlined herein are thoroughly new; nothing of this sort can be detected in products heretofore used in rice weeding and nothing of the like is reported in the literature. Herbicides which had a good selectivity (meaning that they do not permanently damage the useful plants) even in quantities considerably higher than their normal herbicidal doses were known in the past. The product of the present invention exhibits more than mere selectivity (which is substantially a lack of negative biological action towards the useful plant) inasmuch as it exerts a positive biological action which is helpful to the agrarian plant.

Weeding efficiency of M3432 during the pre-emergence stage is high on various graminae and very weak on dicotyledons. The product is not volatile and therefore need not be incorporated or turned into the soil, as is required, on the other hand, by the molinate.

ACTIVITY IN SCREENING CONDITIONS

Example 12

Two sets of small square tanks having 11 cm. sides, filled with field earth admixed with 30% of sand, were sowed at a depth of 0.5–1 cm. with the following grass species: *Echinocloa crus galli*, *Setaria italica*, *Alopecurus myosiuroides*, *Lolium italicum*, *Digitaria sanguinalis*, *Avena fatua*, *Agrostis segetum*, and *Dactylis glomerata*. After sowing, the earth surface of the tanks was uniformly sprayed with 2.4 cc./tank of hydroacetone solutions containing, respectively, 0, 0.05, 0.10, 0.20 and 0.30% of M3432 and of molinate, respectively, in order to obtain doses thereof corresponding to 0, 1, 2, 4, and 6 kg./ha., respectively.

Only one set of small tanks was covered with a 1 cm. layer of earth just after the treatment. All of the tanks were kept in an air-conditioned chamber identical with that described in Example 7, and were watered every day. 25 days after the treatment, the final results were examined, attributing to each treatment the following scale of values:

0 = regular emergence and development;
1 = slightly poorer emergence and development than the control;
2 = moderate activity with partial damage which still does not in general jeopardize the plant's life;
3 = considerable activity causing a damage which definitely jeopardizes the further growth of most of the plants (activity useful for practical utilizations); and
4 = thorough prevention of the emergence, or stopping of the development at 0.5 cm. and successive death of the plants.

Table 8 contains the relevant data.

TABLE 8

| Treatment | Product | Concentration kg./ha. | Weeding activity (infesting plants) | | | | | | | |
|---|---|---|---|---|---|---|---|---|---|---|
| | | | Echinocloa spp. | Setaria sp. | Alopecurus sp. | Lolium sp. | Digitaria sp. | Avena fatua | Agrostis sp. | Dactylii sp. |
| Surface | M3432 | 6 | 4 | 4/3 | 4 | 4 | 4 | 3 | 4 | 4 |
| | | 4 | 4/3 | 4/3 | 3 | 4 | 4 | 3 | — | 4/3 |
| | | 2 | 3/4 | 3 | 2 | 4 | 4 | 3 | 4 | 4 |
| | | 1 | 3 | 3 | 1/2 | 4 | 3 | 2/3 | 4 | 3/4 |
| | Molinate | 6 | 1/2 | 0/1 | 3 | 2/3 | 4 | 4/3 | 4 | 3 |
| | | 4 | 1/2 | 0/1 | 2 | 2 | 3/4 | 3/2 | 4 | 1/2 |
| | | 2 | 2 | 0/1 | 1/2 | 0/1 | 0 | 1 | 2 | 1/2 |
| Treated surface covered with 1 cm earth layer | M3432 | 6 | 4 | 4 | 4 | 4 | 4 | 4 | 4 | 4 |
| | | 4 | 4 | 4/3 | 4 | 4 | 4 | 4 | 4 | 4 |
| | | 2 | 4/3 | 3/4 | 4 | 4 | 4 | 4 | 4 | 4 |
| | Molinate | 6 | 3/4 | 3 | 4/3 | 4 | 4 | 4 | 4 | 4/3 |
| | | 4 | 3 | 3 | 4/3 | 3/4 | 4 | 4 | 4 | 4/3 |
| | | 2 | 3 | 3 | 3 | 3/2 | 4 | 4 | 4 | 3 |

ACTIVITY IN FLOODED CULTURES

In flooded cultures, M3432 exerts on *Echinocloa spp.* in pre-emergence a high degree of activity, at least of the same order as that exerted by molinate. The Echinocloa plants emerge from the soil, but their growth is then stopped between 0.5 and 6 cm., depending upon the M3432 doses and the type of formulation the plants were given. In every case, rotting and death followed.

Example 13

The same method described in Example 7 was adopted, the only variations being the doses (0, 0.5, 1, 2 and 4 kg./ha.), the type of formulation and the sowing of *Echinocloa spp.* (25 slightly pre-germinated seeds per pot) instead of rice. The results are reported in Tables 9–11.

TABLE 9

Test No. 1 — Results gathered 22 days after treatment

| Treatment | Stand (Sprouted plants) (%) | Main root (cm.) | Shoot (cm.) | Remarks |
|---|---|---|---|---|
| Control | 84 | 5.5 | 11.7 | Alive plants |
| M3432, hydroacetone solution, 4 kg./ha. | 0 | 0 | 0 | small plants stopped at 1.5–3 cm., and then died |
| 2 kg./ha. | 0 | 0 | 0 | |
| Molinate, hydroacetone solution, 4 kg./ha. | 0 | 0 | 0 | small plants stopped at 1.5–3 cm., and then died |

TABLE 10

Test No. 2 — Results gathered 21 days after the treatment

| Treatment | Stand (%) | Main root (cm.) | Shoot (cm.) | Remarks |
|---|---|---|---|---|
| Control | 86 | 4.63 | 13.50 | Alive plants |
| M3432, hydroacetone solution, 2 kg./ha. | 0 | 0 | 0 | small plants stopped at 2–5 cm. height and then died |
| 1 kg./ha. | 0 | 0 | 0 | |
| 0.5 kg./ha. | 62 | 3.28 | 8.81 | Alive plants |

TABLE 11

Test No. 3 — Results gathered 27 days after the treatment

| Treatment | Stand (%) | Main root (cm.) | Shoot (cm.) | Remarks |
|---|---|---|---|---|
| Control | 80 | 0.03 | 15.66 | Alive plants |
| M3432, hydroacetone solution, 4 kg./ha. | 0 | 0 | 0 | small plants, stopped at 0.5 cm., and then dried |
| 2 kg./ha. | 0 | 0 | 0 | |
| M3432, 50% emulsifiable oil, 4 kg./ha. | 0 | 0 | 0 | small plants, stopped at 2–3 cm., and then died |
| 2 kg./ha. | 0 | 0 | 0 | |

Example 14

The same method described in Example 9 was followed, the only variation being in sowing *Echinocloa spp.* (40 slightly pregerminated seeds per box) instead of rice.

24 Days after the treatment, the results were observed. The resulting values are reported in Table 12 below.

TABLE 12

| Treatment | Stand (%) | Shoot (cm.) | Remarks |
|---|---|---|---|
| Control | 98.7 | 15.4 | All plants alive |
| M3432, 2 kg./ha. | 2.5 | 8.5 | 1 plant only was alive |
| 4 kg./ha. | 0 | 0 | |
| 6 kg./ha. | 0 | 0 | |
| 8 kg./ha. | 0 | 0 | |

After the *Echinocloa spp.* plants were killed, a second sowing with grass was carried out in the same boxes, 24 days after the treatment, employing 20 slightly pre-germinated seeds per box. The results collected after an additional 24 day period, are reported in Table 13.

TABLE 13

| Treatment | Stand (%) | Shoot (cm.) | Remarks |
|---|---|---|---|
| Control | 100 | 27.5 | All plants alive |
| M3432, 2 kg./ha. | 100 | 26.5 | All plants alive |
| 4 kg./ha. | 65 | 27.0 | 13 plants alive |
| 6 kg./ha. | 0 | 0 | |
| 8 kg./ha. | 0 | 0 | |

Example 15

A clear confirmation of the efficiency of M3432 towards *Echinocloa spp.* was obtained outdoors, where the test was carried out under conditions which are characteristic of Italian rice growing. The experimental conditions are described in Example 10.

36 Days after treatment, the data set forth in Table 14 was observed.

TABLE 14

| Treatment | Infestation degree due to | | |
|---|---|---|---|
| | Echinocloa spp. | Alisma sp. | Scirpus sp. |
| Control | considerable | moderate | moderate |
| Molinate, 4 kg./ha. | almost nil | moderate | moderate |
| M3432 4 kg./ha. | nil | low (°) | low (°) |
| 6 kg./ha. | nil | low (°) | low (°) |

(°) The limited presence of Alisma sp. and of Scirpus sp. in the plots treated with M3432 is ascribable, at least partially, to the particular bloom of the rice which choked such infesting plants after their sprouting.

It should be noted that only the levee of the plots treated with M3432 were thoroughly free from barnyard grass.

2 Months after the treatment, the following was noticed:

Considerable = 10–15 plants per m$^2$
moderate = 1 – 4 plants per m$^2$
low = 0.5–1 plants per m$^2$
almost nil = 0.1 plants per m$^2$

TABLE 15

| Treatment | Infestation degree due to Echinocloa spp. Plants per 10 square meters (no.) |
|---|---|
| Control | 150 |
| Molinate, 4 kg./ha. | 1-2 |
| M3432, 4 kg./ha. | 0.25 |
| 6 kg./ha. | 0.33 |

Example 16

This example demonstrates that M3432 exerts a considerable effect on *Echinocloa spp.* in post emergence.

Test No. 1

A set of boxes having a 1,000 cm$^2$ internal surface was prepared in a hothouse according to the method described in Example 9. The boxes were sowed with *Echinocloa spp.* (70 seeds per box). After saturation of the soil, and as soon as the infesting plants emerged from the soil, the boxes were flooded with a 7 cm. layer of water. When the plants reached a maximum height of 3–4 cm., the treatment was effected by spraying the flooding water surfaces with hydroacetone solutions according to the modalities employed in Example 9. 3 days after the treatment, the following results were observed:

TABLE 16

| Treatment | Stand (%) | Shoot (cm.) | Remarks |
|---|---|---|---|
| Control | 64 | 25-30 | All plants alive |
| M3432, 4, 6, and 8 kg./ha. | 0 | 0 | Maximum height: 3-4 cm.; rotting |

Test No. 2

A second test was carried out in the same manner as Test No. 1 except that the treatment took place when the infesting plants had reached a maximum of 10 cm. 26 days after such treatment, the following was observed:

TABLE 17

| Treatment | Stand (%) | Shoot (cm.) | Remarks |
|---|---|---|---|
| Control | 66.5 | 25-32 | All plants alive |
| M3432, 4, 6, and 8 kg./ha. | 0 | 0 | Maximum height: 10 cm.; rotting |

Test No. 3

Some plots, 12 m$^2$ each, delimited by artificial levees, were prepared outdoors. AFter soil working and grading, the plots were sowed with *Echinocloa spp.* on May 18, 1970 and then flooded to a height of 10 cm. with water on May 20, 1970. The same day, rice was sowed in quantities corresponding to 150 kg. of seed per ha. Both rice and *Echinocloa* emerged from the soil 5 days after the flooding.

When the barnyard grass reached an average height of 12-14 cm., the treatment was effected by uniformly spraying the flooded water surface.

Products being tested: M3432 and molinate, in emulsifiable oil base.

Doses: 0, 4, and 6 kg./ha.

The first effects on *Echinocloa spp.* were noticed for both products 7 days after treatment, 45 Days after treatment the following was observed:

TABLE 18

| Treatment | Rice | Echinocloa spp. |
|---|---|---|
| Control | 35-40 cm. high in normal shooting; partly suffering owing to the presence of the infesting plants | Several plants 15-50 cm. high |
| M3432 4 kg./ha. | Stronger and thicker than the control and than the rice treated with molinate | Complete killing of the previously existing plants; no new emergence |
| M3432 6 kg./ha. | Stronger and thicker than the control and than the rice treated with molinate | Complete killing of the previously existing plants; no new emergence |
| Molinate 4 kg /ha. | Stronger than the control | Complete killing of the previously existing plants; no new emergence |
| Molinate, 6 kg./ha. | Stronger than the control | Complete killing of the previously existing plants; no new emergence |

EXAMPLE 17

This example demonstrates that M3432 in exerting its weed killing action, not only does not damage the rice, but also stimulates its development, even when the product is distributed on the seed surface before sowing.

Test No. 1

A set of glass pots was prepared as described in Example 7. Immediately after such preparation the pots were filled with water to a level of 7 cm. above the ground surface. Cv. RIBE rice seeds, which were previously allowed to swell in water, were divided into four groups. Each group was treated, by application with a micro syringe with a quantity of M3432 composition; containing 70% active product, corresponding to the following doses of a.p. per ha.: 0, 2.5, 5, and 10 kg. seeds coated with the compound were placed into each pot and subsequently covered with a thin layer of earth. After 41 days, the following results were obtained.

TABLE 19

| Treatment | Stand (%) | Main root (cm.) | Shoot (cm.) | Secondary roots (no.) |
|---|---|---|---|---|
| Control | 55.50 | 7.92 | 11.97 | 3.11 |
| M3432 2.5 kg./ha. | 68.80 | 8.93 | 17.16 | 3.90 |
| 5 kg./ha. | 62.20 | 8.48 | 16.83 | 4.02 |
| 10 kg./ha. | 62.20 | 10.07 | 16.92 | 4.23 |

Test No. 2

A similar test was conducted outdoors on clay soil, operating on 12 square meter plots delimited by artificial, waterproof levees.

After flooding, the plots were sowed broadcast with seeds treated as in Test No. 1 with doses corresponding, respectively, to 0, 5 and 10 kg./ha. In all cases the quantity of seed amounted to 150 kg./ha. 45 days after sowing, the following was ascertained:

TABLE 20

| Treatment | Infestation degree due to Echinocloa spp. | Rice plants |
|---|---|---|
| Control | Many plants about 40 cm. high | Several plants about 40 cm. high |
| M3432 5 kg./ha. | All plants stopped growing at 1 cm. height and then died | Several plants about 50 cm. high and very strong |
| 10 kg./ha. | All plants stopped growing at 1 cm. height and then died | Several plants about 60 cm. high and very strong |

Test No. 3

A further test was carried out outdoors on loam soil on plots of about 5000 square meters surface.

After flooding each plot, seeds treated as in Test No. 1 with doses corresponding to 0, 3, and 4 kg./ha. were mechanically sowed broadcast. In all cases, the seen quantity was 150 kg./ha. 67 days after sowing, the results were gathered on 5 representative testing areas of 1 square meter each for each dosage level. Table 21 below contains a summary of the results.

TABLE 21

| Treatment | Rice Tiller (no.)/m² | Rice Tiller dry weight (g.)/m² | Barnyard grass Tiller (no.)/m² |
|---|---|---|---|
| Control | 351 | 252.20 | 23 |
|  | 145 | 94.80 | 99 |
| (Rice field area: 3000 m²; data for 5 random 1 m² plots) | 233 | 143.53 | 103 |
|  | 180 | 120.20 | 100 |
|  | 240 | 169.63 | 50 |
| Average on 5 testing areas for the control | 229.8 | 156.07 | 75.0 |
| M3432 - 3.4 kg./ha. | 432 | 254.50 | 0 |
|  | 430 | 331.10 | 0 |
| (Rice field area: 4800 m²) | 421 | 301.08 | 0 |
|  | 417 | 373.50 | 0 |
|  | 392 | 332.00 | 0 |
| Average on 5 testing areas for M3432-3.6 kg./ha. | 418.4 | 318.44 | 0 |
| M3432 - 4.0 kg./ha. | 599 | 473.98 | 0 |
|  | 440 | 316.91 | 0 |
| (Rice field area: 5400 m²) | 687 | 484.50 | 0 |
|  | 523 | 423.55 | 0 |
|  | 546 | 491.10 | 0 |
| Average on 5 testing areas for M3432-4.0 kg./ha. | 559.0 | 438.01 | 0 |
| LSD* (.05) | 86.0 | 89.51 |  |
| (.01) | 125.1 | 130.24 |  |

*LSD Least Significant Difference.

The possibility of weeding the rice fields by distributing the herbicide together with the seed during the sowing, that is, the possibility of utilizing the seed as a "carrier" for the herbicide (see Example 17), must be considered a particularly exceptional experimental development. This means of utilization of the herbicide of the present invention allows, in fact, the achievement of a considerable technical simplification, combining sowing and weeding in a single operation. The resulting economy is particulary advantageous for the wide rice growing areas where sowing operations and weed killing treatments are carried out by airplane.

To the several exceptionally favorable characteristics exhibited by the product of the present invention, discussed above, a further extraordinarily important property, namely the absence of any toxicity towards warm blooded animals must be added. Thus M3432, whose acute toxicity towards rats per os $LD_{50}$ is 10,250 mg./kg. and towards mice is 8,000 mg./kg., is to be considered in practice as non-toxic, particularly in comparison with the actual toxicity values indicated in the literature and summarized in Table 22 below for the main prior art herbicides used or suggested to kill the graminae in rice fields.

TABLE 22

| Herbicide | ACUTE TOXICITY rats, os $LD_{50}$ mg./kg. | mice, os $LD_{50}$ mg./kg. |
|---|---|---|
| Molinate | 500–725 |  |
| Propanil | 1384 |  |
| Swep | 552 |  |
| Pentachlorophenol | 78–280 |  |
| Saturn |  | 560 |
| Nitrofen | 3000 |  |

Molinate is ethyl-1-hexamethyleneimino carbothiolate;
Propanil is N(3,4-dichlorophenyl)-propionamide;
Swep is methyl-N-(3,4-dichlorophenyl)carbamate;
Saturn is S(4-chlorobenzyl)N,N-diethylthiocarbamate;
Nitrofen is 2,4-dichlorophenyl-4'-nitrophenylether.

For weeding or for stimulating the rice growth, the product of the present invention can be prepared in a suitable treating composition without any difficulty, using solid or liquid diluents, solvents, emulsifying agents, and dispersants in order to obtain compositions or formulations fit for being stored, handled and, if necessary, further diluted to the required concentration for utilizing in the fields.

Formulations may be prepared in solid, granulated, or liquid form or in the form of pastes of various concentrations. Depending upon the ambient conditions and the technical means available, one type of composition rather than another may be preferred.

Solid compositions in the form of pellets are prepared either by intimately mixing the dry, active product with inert solid carriers such as bentonite, calcite, dolomite, vermiculite, attapulgite, pyrophyllite, sepiolite, phosphorite, kieselguhr, hydrated silica and synthetic calcium silicates, as well as with fertilizers such as ammonium sulphate, urea, phosphorite, superphosphates, complex fertilizers, etc., with optional addition of a surfactant, or by causing the carriers to absorb a solution of the active compound.

An example of a suitable granulated formulation is the following:

M3432 — 5% by weight;
Bentonite 16/40 mesh — 94% by weight
Surfactant comprising sodium iso-octylsulphosuccinate — 1 % by weight.

In preparing the formulation, the active compound and the surfactant are mixed with the minimum quantity of methylene chloride necessary to wet all of the bentonite and the mass is mixed in a mixer provided with a vapor suction device, until all the methylene chloride has evaporated.

The active product content of the granulated formulation may vary within wide limits, for example, between about 0.25% and about 80%, preferably between about 0.50% and about 20% (by weight). The size of the granulated carrier particles may be between about 0.1 mm. and about 4 mm., preferably between about 0.15 mm. and about 0.7 mm.

The so-called "wettable powders" are obtained by admixing one or more surfactants with the powders.

By dispersing such wettable powders in water, aqueous suspensions of the desired concentrations are obtained. Such aqueous suspensions are sprayed on the soil. An example of a suitable wettable powder is the following:

M3432 — 40% (by weight);
Celite-209 CYA by Johns Mansville Italiana — 53% (by weight);
Atlox 4860 by Atlas Chem. Ind. — 4% (by weight)
Geropon TA 72 by Geronazzo — 3% (by weight).

Emulsifiable liquid formulations (emulsifiable concentrates) are prepared by dissolving the active compound in a solvent or mixture of solvents which are insoluble in water and by adding one or more surfactants.

The active compound content of these formulations ranges from about 70 to about 15% by weight. When these compositions are admixed with water, emulsions are obtained in which the solvent phase is dispersed in the aqueous phase and the active product is kept in solution in the dispersed phase. In this way it is possible to obtain a uniform distribution of the active product in the aqueous compositons used for spraying.

The following is an example of a suitable emulsifiable liquid formulation:

M3432 — 50% (by weight);
Xylol — 25%;
Tetrachloroethylene — 15%;
Mixture of organic, vegetable ethoxylated sulfonates — 10%.

An example of another concentrated liquid formulation which can be sprayed directly onto the rice seeds is the following:

M3432 — 70% (by weight);
APA 106 by D.A.C. — 30%.

As emulsifying dispersing agents (surfactants) which are employed for preparing wettable powders and emulsifiable concentrates, surfactants of the anionic, nonionic, and cationic types can be used.

Suitable surfactants of the anionic type include sodium dodecyl-benzene-sulfonate, calcium naphthalene-sulfonate, and sodium lauryl-sulfate; suitable surfactants of the cationic type include quaternary ammonium compounds such as cetylpyridinium bromide, dodecyl-benzyl-methyl-ammonium chloride, and di-(hydroxy-ethyl)-benzyldodecylammonium chloride; suitable nonionic surfactants include the condensation products of ethylene oxide with aliphatic alcohols, amines, fatty acids, and alkyl phenols.

Owing also to the excellent solubility exhibited by the compound of this invention in a large number of solvents, the preparation of any type of composition containing it presents no difficulties; herbicides exerting a complementary action, or algacides, pesticides, fertilizers and the like, may be incorporated in the compositions, if desired.

The use of the compound of the present invention in any type of composition for weeding — independent of the techniques adopted — is within the contemplation and scope of the present invention.

The quantities of weeding composition employed to carry out the weeding vary considerably according to the active compound concentration, the plant species, and the treatment technique. On the average, these quantities should be such as to apply from about 2 to about 8 kg./ha. of soil.

If one wants to obtain an enhanced stimulating effect, greater than that obtainable with the doses sufficient for weeding, doses even higher than the ones indicated may be employed, for example, 30 kg./ha. or even higher.

Variations can, of course, be made without departing from the spirit and scope of this invention.

What we desire to secure by Letters Patent and hereby claim is:

1. A composition for controlling and killing rice field weeds and simultaneously stimulating the growth of rice, said composition comprising an effective amount of S-benzyl N,N-disec.butyl-thiocarbamate and an inert vehicle therefor.

2. A method for controlling rice field weeds and stimulating the growth of rice, said method comprising applying to a rice field an amount of S-benzyl-N,N-disec. butyl-thiocarbamate which is effective to simultaneously control rice field weeds and stimulate the growth of rice.

3. The method of claim 2 wherein the S-benzyl-N,N-disec. butyl-thiocarbamate is employed in a composition containing a product selected from the group consisting of a solid carrier and a liquid solvent or dispersion medium therefor.

4. The method of claim 2 wherein the S-benzyl-N,N-disec.butyl-thiocarbamate is applied to the rice field before germination of the rice.

5. The method of claim 2 wherein the S-benzyl-N,N-didec.butyl-thiocarbamate is applied to the rice field after germination of the rice.

6. The method of claim 2 wherein the S-benzyl-N,N-disec.butyl-thiocarbamate is applied to the rice field in the form of an aqueous dispersion.

7. The method of claim 2 wherein the S-benzyl-N,N-disec.butyl-thiocarbamate is applied to the rice field in the form of an aqueous emulsion.

8. The method of claim 3 wherein the S-benzyl-N,N-disec.butyl-thiocarbamate composition is in the form of a paste.

9. The method of claim 2 wherein the S-benzyl-N,N-disec.butyl-thiocarbamate is applied to the rice field in the form of dry powder or pellets.

10. The method of claim 2 wherein the S-benzyl-N,N-disec.butyl-thiocarbamate is applied to the rice field by coating pre-soaked rice seeds therewith and thereafter sowing the coated rice seeds in the rice field.

11. The method of claim 3 wherein the carrier is selected from the group consisting of bentonite, calcite, dolomite vermiculite, attapulgite, pyrophyllite, sepiolite, phosphorite, kieselguhr, hydrated silica and synthetic calcium silicates.

12. The method of claim 2 wherein said amount is between about 2 and about 30 kg./ha.

13. The method of claim 2 wherein said amount is between about 2 and about 8 kg./ha.

14. The composition of claim 1, wherein the inert vehicle is selected from the group consisting of water, organic solvents for said S-benzyl-N,N-disec.butyl-thiocarbamate, and solid carriers compatible therewith.

* * * * *

UNITED STATES PATENT OFFICE
CERTIFICATE OF CORRECTION

Patent No. 3,930,838          Dated January 6, 1976

Inventor(s) GIOVANNI PELLEGRINI et al

It is certified that error appears in the above-identified patent and that said Letters Patent are hereby corrected as shown below:

Column 1, lines 7-14:
"     BACKGROUND OF THE INVENTION

1. Field of the Invention
 This is a continuation of application Ser. No. 178,662, filed Sept. 8, 1971 and now abandoned."
should read:
--     CROSS REFERENCE TO RELATED APPLICATIONS
 This is a continuation of application Ser.No. 178,662, filed Sept. 8, 1971 and now abandoned.

BACKGROUND OF THE INVENTION
 1. Field of the Invention --.

Column 1, line 62:  "casue" should read -- cause --.

Column 2, line 27:  "gotting" should read -- gotten --.

Column 4, line 68:  "water introduced" should read -- water were introduced --.

Column 6, line 31:  "hereinafter" should read -- (hereinafter --.

Column 12, last column of Table 8:  "Dactylii sp." should read -- Dactylis sp. --.

UNITED STATES PATENT OFFICE
CERTIFICATE OF CORRECTION

Patent No. 3,930,838    Dated January 6, 1976

Inventor(s) GIOVANNI PELLEGRINI et al

It is certified that error appears in the above-identified patent and that said Letters Patent are hereby corrected as shown below:

Column 12, line 56: "Echinocloa" should read -- *Echinocloa* --.

Column 15, lines 17-21: These lines should be footnotes to Table 14.

Column 16, line 25: "AFter" should read -- After --.

Column 17, line 50: "seen" should read -- seed --.

Signed and Sealed this twentieth Day of April 1976

[SEAL]

Attest:

RUTH C. MASON
Attesting Officer

C. MARSHALL DANN
Commissioner of Patents and Trademarks